US00PP23648P2

(12) United States Plant Patent
MacKenzie

(10) Patent No.: US PP23,648 P2
(45) Date of Patent: May 28, 2013

(54) ***SEDUM* PLANT NAMED 'NONEN'**

(50) Latin Name: *Sedum reflexum*
Varietal Denomination: Nonen

(75) Inventor: David MacKenzie, Nunica, MI (US)

(73) Assignee: Hortech, Inc., Spring Lake, MI (US)

( * ) Notice: Subject to any disclaimer, the term of this patent is extended or adjusted under 35 U.S.C. 154(b) by 84 days.

(21) Appl. No.: 13/200,428

(22) Filed: Sep. 23, 2011

(51) Int. Cl.
*A01H 5/00* (2006.01)

(52) U.S. Cl.
USPC ..... Plt./479

(58) Field of Classification Search ..... Plt./479
See application file for complete search history.

*Primary Examiner* — Susan McCormick Ewoldt
(74) *Attorney, Agent, or Firm* — Penny J. Aguirre

(57) ABSTRACT

A new cultivar of *Sedum* plant, 'Nonen', characterized by its evergreen vibrant spring green foliage which stays this color summer, fall, and winter. Its flowers of early summer are bright lemon yellow upon erect flat-topped inflorescences, atop stout, leafy, upright floral stems that emerge from a low growing procumbent plant habit.

1 Drawing Sheet

Botanical classification: *Sedum reflexum.*
Variety denomination: 'Nonen'.

CROSS REFERENCE TO A RELATED APPLICATION

This application is co-pending with a U.S. Plant Patent Applications that pertain to plants derived from the same parentage, the Applications are entitled *Sedum* Plant named 'Nonah' (U.S. Plant Pat. No. 23,393), *Sedum* Plant named 'Nonal' (U.S. Plant Pat. No. 23,412), *Sedum* Plant named 'Nonar' (U.S. Plant Pat. No. 23,392), *Sedum* Plant named 'Noneb' (U.S. Plant Pat. No. 23,413), *Sedum* Plant named 'Nonic' (U.S. Plant Pat. No. 23,394), *Sedum* Plant named 'Nonist' (U.S. Plant Pat. No. 23,411), *Sedum* Plant named 'Nonot' (U.S. Plant Pat. No. 23,312), *Sedum* Plant named 'Noniw' (U.S. Plant patent application Ser. No. 13/200,692), *Sedum* Plant named 'Nonow' (U.S. Plant Pat. No. 23,323), and *Sedum* Plant named 'Nonul' (U.S. Plant Pat. No. 23,381).

BACKGROUND OF THE INVENTION

During the last several decades, botanists and horticulturists have disagreed as to whether the species *Sedum reflexum* and *Sedum rupestre* are truly distinct. An examination of today's most useful literature (Handbook of Cultivated *Sedums* by Ronald L. Evans, and *Sedum* Cultivated Stonecrops by Ray Stephenson) are no different. Evans treats them as distinct species and Stephenson refers to them as synonymous and correctly identified as *Sedum rupestre*. The Applicant, a biologist, sides with Evans, and believes that there are sufficient morphological differences between the two plants as to be easily distinguished and to warrant recognition as two distinct species. Therefore, because the subject plant of this application is the result of cross breeding two cultivars, which conform to Evans description of *Sedum reflexum* (most notably foliage that covers the entire length of the stem, vs. just the distal end), the species, throughout this application, is referred to as *Sedum reflexum.*

The present invention relates to a new and distinct cultivar of *Sedum* plant, botanically known as *Sedum reflexum*

'Nonen' and will be referred to hereinafter by its cultivar name, 'Nonen'. The new cultivar of *Sedum* is a hardy herbaceous perennial grown for use as a landscape and container plant and is particularly suitable as a ground cover 'Nonen' was selected as a single unique plant in March of 2009 from amongst 10,000 seedlings that arose from a deliberate cross between *Sedum reflexum* 'Angelina' (not patented) as the female parent and an unnamed plant of *Sedum reflexum* as the male parent.

Asexual reproduction of the new cultivar was first accomplished by stem cuttings in August of 2009 in Nunica, Mich. Propagation by cuttings and crown division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Nonen' as a unique cultivar of *sedum.*

1. 'Nonen' exhibits foliage that emerges vibrant spring green and holds this color during summer, fall, and winter.
2. 'Nonen' exhibits flower buds that are bright yellow.
3. 'Nonen' exhibits flat topped, somewhat drooping inflorescences with flowers of bright lemon yellow during early summer.
4. 'Nonen' exhibits a dense, low growing habit with foliage that reaches 5 inches in height.

The male parent, an unnamed plant of *Sedum reflexum*, differs from 'Nonen' in having gray-blue foliage during spring, summer, fall and winter. The female parent, 'Angelina', differs in having chartreuse foliage that turns variably yellow, amber, or orange during the fall and winter. 'Nonen' can be compared to other cultivars of *Sedum reflexum* (all are un-patented), which differ from 'Nonen' in the following characteristics: 'Green Spruce'; a weak grower that is colored dark green during spring summer and fall, and burgundy-green during winter, 'Sea Gold'; a weak growing cream and gray-blue variegated cultivar, and 'Sandy's Silver Crest'; a form that turns purple in strong sunlight and has new growth of contrasting yellow-white.

'Nonen' can be compared to other cultivars selected amongst seedlings from the same cross; 'Nonist', 'Nonah', 'Nonal', and 'Nonar', 'Nonul', 'Nonot', 'Noneb', 'Nonic', 'Noniw', and 'Nonow', 'Nonist' differs from 'Nonen' by having leaves that emerge blue-gray and change to blue-green in maturity before becoming suffused with red-purple during fall and winter. Its habit reaches 6 to 7 inches tall. 'Nonah' differs from 'Nonen' by having leaves that emerge yellow-green often variably suffused with purple-red and holds this color throughout summer. During fall and winter the purple red hues intensify. Its growth habit 6 inches tall. 'Nonal' differs from 'Nonen' in having leaves that emerge clear yellow and stay clear yellow throughout summer. During late fall and winter it becomes variably suffused with red-purple. Its growth habit reaches 5 inches tall. 'Nonar' differs from 'Nonen' in that it has leaves that emerge bright yellow and stay bright yellow color until fall and winter when they change to hues of burnt orange. The exception is the leaves on the lower ⅔ of the floral stem which are suffused with burnt orange during the summer. Its growth habit reaches 4 inches tall. 'Nonul' differs from 'Nonen' by having leaves emerge pale bluish-green and stay pale bluish-green throughout summer. During fall and winter the leaves become variably suffused with grayed-purple hues. Its growth habit reaches 5 inches tall. 'Nonot' differs from 'Nonen' by having leaves that emerge chartreuse-yellow and stay chartreuse-yellow throughout summer. During fall and winter the leaves become variably suffused with red-purple. Its growth habit reaches 7 inches tall. 'Noneb' differs from 'Nonen' by having leaves that emerge gray-green and mature to medium blue variably suffused with red-purple before changing predominantly to red-purple during late fall and winter. Its growth habit reaches 5 inches tall. 'Nonic' differs from 'Nonen' by having leaves that emerge sky blue and stay sky blue during summer until fall when they change to violet-blue. Its growth habit reaches 4 inches tall. 'Noniw' differs from 'Nonen' by having leaves that emerge bright yellow, mature to light green during summer, then become red-tipped during fall and winter. Its growth habit reaches 5 inches tall. 'Nonow' differs from 'Nonen' by having leaves that emerge chartreuse and mature to mid-green and stays mid-green throughout summer, fall and winter. Its growth habit reaches 7 inches in height. All eleven cultivars have flat-topped, somewhat dropping inflorescences, borne on leafy upright stems. All have flower buds that are bright yellow and flower petals that are bright lemon yellow.

BRIEF DESCRIPTION OF THE DRAWINGS

The accompanying colored photograph illustrates the overall appearance and distinct characteristics of the new *Sedum*.

The photograph was taken of a 2 year-old plant of 'Nonen' as grown in the ground in full sun in Nunica, Mich.

The photograph in FIG. 1 illustrates the summer foliage of 'Nonen'.

The colors in the photograph may differ slightly from the color values cited in the detailed botanical description, which accurately describe the colors of the new *Sedum* using The R.H.S. Colour Chart.

DETAILED BOTANICAL DESCRIPTION

The following is a detailed description of the new cultivar as observed on 2 year-old plants of 'Nonen' as grown in the ground in full sun in Nunica, Mich. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period.*—The last two to three weeks of June to the first or second week of July in Michigan.

*Plant habit.*—Herbaceous perennial, dense, low growing habit, mature plant sprawl from central crown with procumbent stems rooting as they contact the ground.

*Height and spread.*—Reaches about 5 inches in height (foliage), 12 inches in bloom, maximum spread in about 22 inches.

*Hardiness.*—Reliably in U.S.D.A. Zones 4B to 7B.

*Disease and pests.*—No susceptibility or resistance to diseases or pests has been observed.

*Propagation.*—Stem cuttings spring through summer and crown division throughout the year.

*Growth rate.*—Moderate.

Stem description:

*Stem shape.*—Round.

*Stem size.*—4 to 5 inches in length and about ⅛ inch in width.

*Internode length.*—Ranges from 1/16 to ⅛ inch.

*Stem color.*—145A.

*Stem surface.*—Glabrous.

*Branching habit.*—Sparsely branched.

Foliage description:

*Leaf shape.*—Acicular.

*Leaf division.*—Simple.

*Leaf arrangement.*—Alternate.

*Leaf base.*—Connected directly to stem.

*Leaf apex.*—Acute.

*Leaf venation.*—Not conspicuous, color matched leaf color.

*Leaf margins.*—Smooth, young leaves papilose-ciliate.

*Leaf attachment.*—Sessile.

*Leaf presence and orientation.*—Ascending.

*Leaf surface.*—Glabrous and waxy on upper and lower surface.

*Leaf color.*—In youth and maturity leaves are colored 144C.

*Leaf size.*—Young leaves; an average of ¼ inch length and 1/16 inch in width, mature leaves; an average of ¾ inches in length and ⅛ inches in width.

*Petioles.*—⅛ inch in length, 1/16 inch in width, 144C in color, surface is glabrous.

Flower description:

*Inflorescence type.*—Terminal, cymose, drooping and sub-globose in bud, erect and flat in flower, concave in fruit, branches short and forked, dense many flowered, sparingly leafy.

*Inflorescence size.*—An average of 1½ inches in width and ¾ inches depth.

*Lastingness of inflorescence.*—About one month.

*Flower type.*—Perfect, spreading, 6-starred.

*Flower number.*—25 to 35 flowers per cyme.

*Flower fragrance.*—None.

*Flower buds.*—Conical in shape, about ⅜ inch in length and 3/16 inch in diameter, ribbed surface, 7A in color.

*Flower size.*—About ½ inch in length and ¾ inch in diameter.

*Peduncles.*—Round, range from ½ inch to ¾ inches in length, ⅛ inch in width, 145C mixed with 182B in color, glabrous surface with 144C leaves.

*Pedicels.*—Round, range from ⅜ inch to 1 inch in length, 1/16 inch in width, 144-B in color, glabrous surface.

*Sepals.*—6, spreading, ovate to lanceolate in shape, about ⅜ inch in length and ⅛ inch in width, 145C in color on both surfaces, entire margin, acute apex, truncate base, glabrous on both surfaces.

*Petals.*—6, spreading, lanceolate in shape, truncate base, acute apex, entire margin, color of inner and outer surfaces is 12A, glabrous on both surfaces.

Reproductive organs:

*Pistils.*—6, held erect, about ⅜ inch in length, stigma 1/32 inch in width and 151C in color, styles ¼ inch in length and 151C in color, ovary 1/10 inch in diameter and 151C in color.

*Stamens.*—10, about ⅜ inch in length, filament 151D in color, anther 151D in color, pollen is sparse in quantity and 151D in color.

*Fruit.*—Rounded with pointed tip, aggregate, range from 1/16 inch to ⅛ inch in length and ¼ inch in width, 151D in color, seed production was not observed.

It is claimed:

1. A new and distinct variety of *Sedum* plant named 'Nonen' as described and illustrated herein.

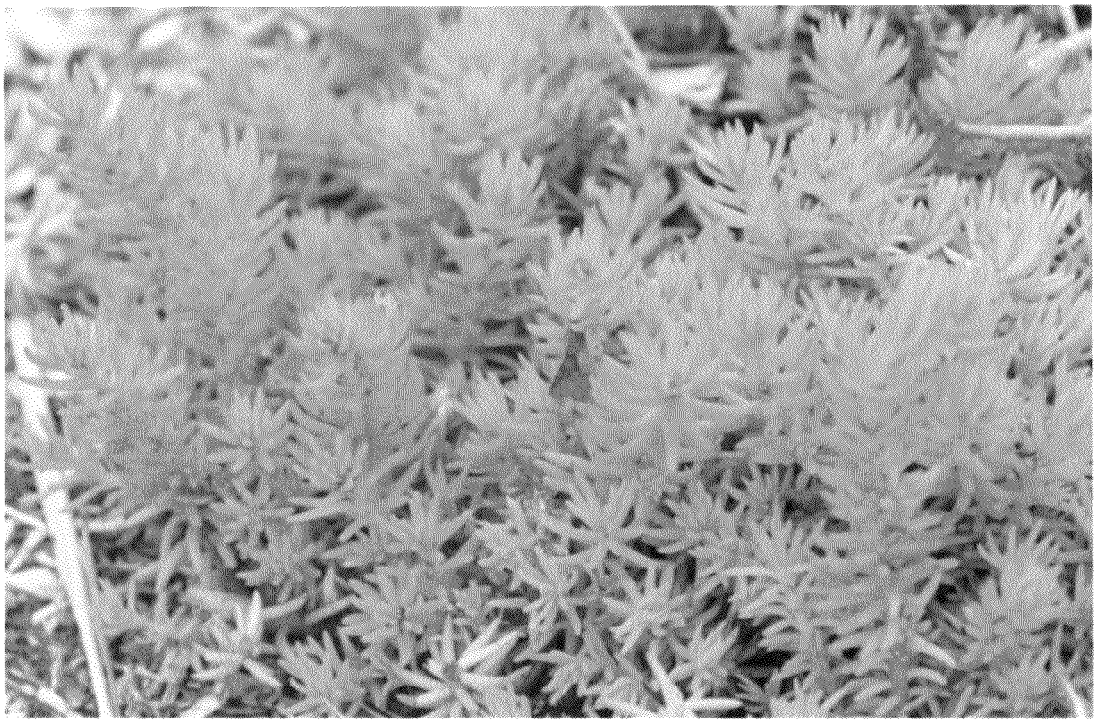

* * * * *